United States Patent [19]

Fargie et al.

[11] Patent Number: 4,736,737
[45] Date of Patent: Apr. 12, 1988

[54] TIBIAL CUTTING JIG

[76] Inventors: William Fargie, 31220 La Baya Dr., No. 110, Westlake Village, Calif. 91362; James Friend, 1921 18th St., Bakersfield, Calif. 93301; John L. Wilson, 11254 Amestoy Ave., Granada Hills, Calif. 91344

[21] Appl. No.: 846,359

[22] Filed: Mar. 31, 1986

[51] Int. Cl.$^4$ .................. A61B 17/00; A61B 17/56; A61F 2/46

[52] U.S. Cl. .................. 128/92 VY; 128/92 YZ; 623/20; 83/829

[58] Field of Search .................. 269/307; 128/92 YV, 128/92 V, 92 VY, 92 VV, 92 VW, 305, 92 YZ; 623/20, 16; 408/14, 202; 409/218; 83/764, 829, 468; 33/567, 568, 570, 573, 628–630, 640; 30/375

[56] References Cited

U.S. PATENT DOCUMENTS

| | | | |
|---|---|---|---|
| 2,156,034 | 4/1939 | Thomas | 33/628 X |
| 2,485,274 | 10/1949 | Garret | 83/468 |
| 2,618,300 | 11/1952 | Freudenthaler | 83/468 |
| 2,980,986 | 4/1961 | Gryglas | 408/202 |
| 3,352,186 | 11/1967 | Cleland | 83/829 X |
| 3,531,870 | 10/1970 | Romancky | 33/630 |
| 4,474,177 | 10/1984 | Whiteside | 128/92 VWX |
| 4,485,704 | 12/1984 | Gardner | 408/14 |
| 4,567,885 | 2/1986 | Androphy | 128/92 VW |
| 4,567,886 | 2/1986 | Petersen | 128/92 VWX |

OTHER PUBLICATIONS

"Knee Replacement Using the Insall/Burstein Total Condylar Knee System", John Insall, Albert Burstein, 1979, pp 1–23, an article published by the New York Society for the Relief of the Ruptured and Crippled.

Primary Examiner—Richard J. Apley
Assistant Examiner—David J. Bender
Attorney, Agent, or Firm—Kelly, Bauersfeld & Lowry

[57] ABSTRACT

An improved tibial cutting jig is provided for use in obtaining accurate tibial resection in the course of a total knee prosthesis implantation procedure. The tibial cutting jig includes a base for sliding reception onto an intramedullary alignment rod preinstalled generally along the longitudinal axis of the tibia. The base includes laterally extending outriggers carrying removable measurement keys of selected size for spacing the base above the tibial plateau by a selected dimension. An anterior saw guide depends from the base and is thus positioned relative to the tibial plateau in accordance with the sizes of the measurement keys.

13 Claims, 1 Drawing Sheet

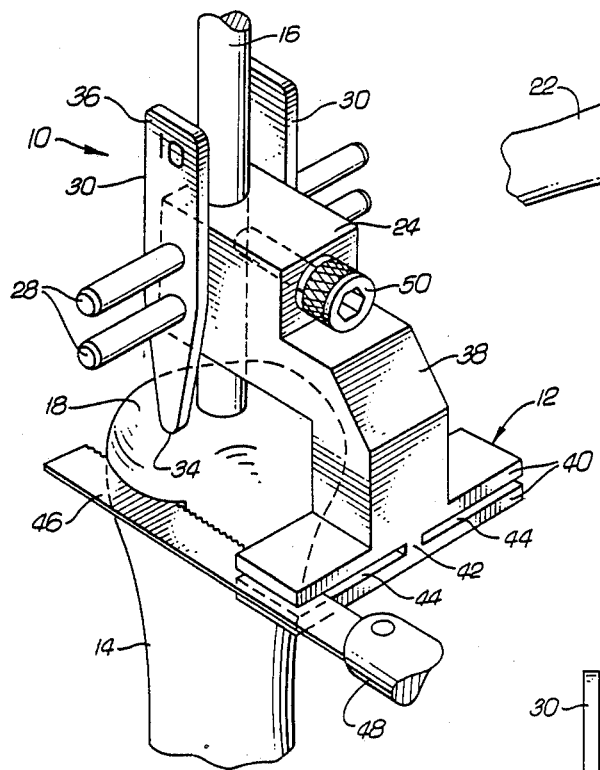
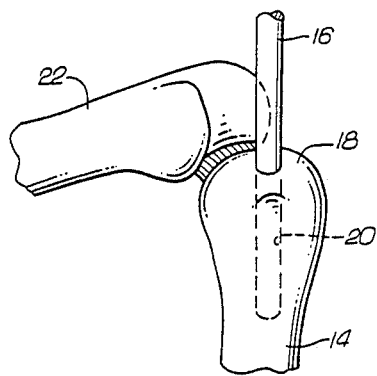
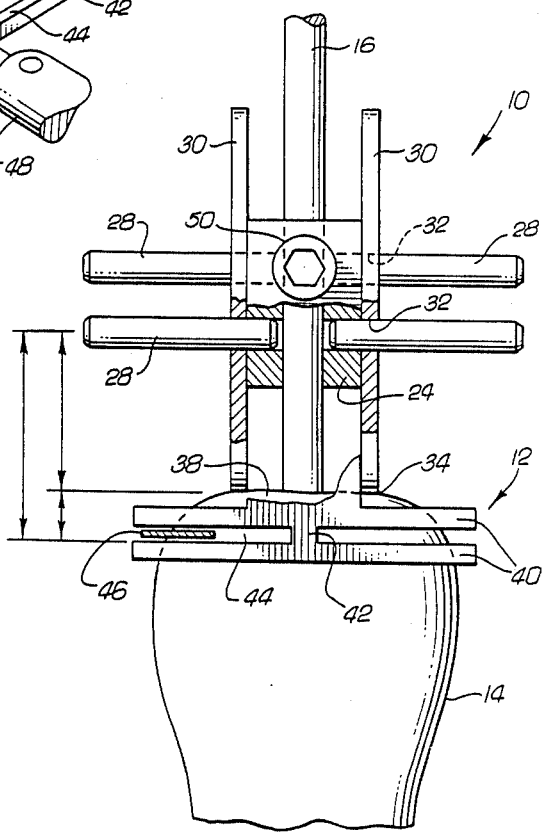
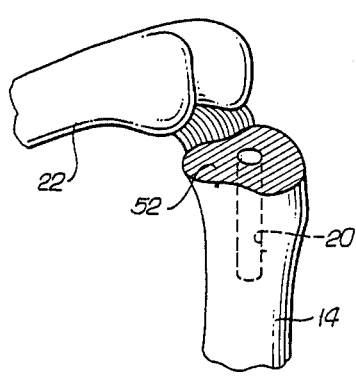

TIBIAL CUTTING JIG

BACKGROUND OF THE INVENTION

This invention relates generally to bone resection apparatus for use in the implantation of artificial joints, such as a total knee prothesis or the like. More particularly, this invention relates to an improved tibial cutting jig for accurate resection of the tibia to insure optimum placement of the tibial component of a total knee prothesis.

Prosthetic joint devices such as total knee protheses are relatively well known in the art for implantation into the body. Such knee protheses typically include a femoral and a tibial component designed for respective affixation to the femur and tibia and further including mating bearing surfaces designed to accommodate articulated knee motion. Component affixation to patient bone has normally required at least some resection and shaping of femoral and tibial surfaces at the knee joint, with the components thereafter being secured to the bone by a press-fit attachment, by use of a selected bone cement, by use of porous bone ingrowth surfaces, or by a combination of these techniques. Exemplary total knee protheses are described in more detail in U.S. Pat. Nos. 4,355,429 and 4,085,466.

In total knee protheses, the complex geometry of the knee joint together with the complex mechanical loading thereof during normal function makes it extremely important for the prosthetic components to be accurately aligned and securely seated on the patient bone. More particularly, the tibial component comprises the primary load bearing component and must be positioned properly on the proximal or upper end of the tibial with minimal shear forces at the prothesis-bone interface. Otherwise, during normal knee function, these shear forces can cause the tibial component to become dislodged resulting in failure of the prothesis, wherein such failure can be repaired, if at all, only by additional surgery.

In the past, various operative procedures have been followed for preparing the tibial proximal end for mounting of the tibial component of a total knee prothesis, wherein such procedures have predominantly envisioned resection of the tibial plateau on a plane generally perpendicular to the tibial longitudinal axis. In accordance with one common technique, this resection has been performed with a power saw along a free hand cut without the use of any saw guide or other measurement/alignment apparatus. However, this approach clearly requires a high degree of surgeon skill to avoid inaccurate resection and frequently requires multiple cuts on a trial and error basis to achieve accurate alignment and seating of the tibial component. Other bone cutting techniques have utilized saw guides mounted on intramedullary femoral alignment rods preinstalled along the femoral longitudinal axis. However, such saw guides have not been applied for use with the tibia and in any event have been adjustably positioned according to measurements referenced from the intramedullary rod. Accordingly, any inaccuracy in placement or settling of the intramedullary rod has resulted in a correspondingly inaccurate resection, thereby frequently requiring a trial and error fitting of the tibial component.

There exists, therefore, a significant need for an improved device for obtaining a precision resection of the tibial plateau in the course of a total knee prosthesis implantation procedure. The present invention fulfills this need and provides further related advantages.

SUMMARY OF THE INVENTION

In accordance with the invention, an improved tibial cutting jig is provided for use in obtaining accurate resection of the tibial plateau during knee prosthesis implantation surgery. The improved cutting jig is designed for mounting upon a preinstalled intramedullary alignment rod and includes means for adjustably positioning a saw guide relative to the tibia with an accurate measurement referenced directly from the tibial plateau.

In the preferred form of the invention, the improved cutting jig includes a base having a vertical bore therein for reception over an intramedullary alignment rod preinstalled generally along the longitudinal axis of the tibia. The base supports outriggers pins projecting outwardly in opposite directions, with said pins preferably being provided in vertically spaced pairs on both sides of the base. Measurement keys are slidably fitted onto the outrigger pins and have lower tips projecting downwardly from the base by selected distances for directly contacting the tibial plateau. A saw guide is also supported by the base in a depending position anteriorly of the tibia and at a vertical position spaced below the tips of the measurement keys by a precision distance indicated by indicia borne by the measurement keys.

In use, a selected set of measurement keys is mounted on the outrigger pins and the base in placed over the intramedullary rod with the key tips seated on the tibial plateau. This positions the saw guide anteriorly of the tibia with a saw guide slot at a selected depth according to the set of measurement keys on the outrigger pins. The base is then locked onto the intramedullary rod by means of a set screw or the like and the tibia is resected accurately using a conventional surgical saw guided by the saw guide slot.

Other features and advantages of the invention will become more apparent from the following detailed description taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a fragmented perspective view illustrating an improved tibial cutting jig embodying the novel features of the invention;

FIG. 2 is a fragmented perspective view illustrating preinstallation of an intramedullary alignment rod;

FIG. 3 is a fragmented front elevation view illustrating use of the tibial cutting jig; and FIG. 4 is a fragmented perspective view illustrating the resected tibial surface.

DETAILED DESCRIPTION OF THE PREFERRED EMBODIMENT

As shown in the exemplary drawings, an improved tibial cutting jig referred to generally by the reference numeral 10 is provided for obtaining accurate tibial resection in the course of a knee prosthesis implantation procedure. The cutting jig 10 includes a saw guide 12 which is accurately and adjustably positioned relative to the tibia 14 of a patient at a cutting depth referenced directly from the tibia 14.

The improved tibial cutting jig 10 of the present invention provides a relatively simple and easy to use apparatus for obtaining accurate resection of the tibia 14 to accommodate secure seated implantation of the tibial load bearing component of a total knee prothesis (not shown). More particularly, the cutting jig 10 is designed for easy mounting onto a conventionally preinstalled intramedullary alignment rod 16 protruding upwardly from the tibia 14 generally along the longitudinal axis of the tibia. However, the improved jig 10 of the present invention does not position the saw guide 12 in accordance with a measurement referenced from the intramedullary rod 16, but instead positions the saw guide according to a measurement referenced directly from the tibial plateau 18. Advantageously, this measurement can be varied as required to suit individual patient size requirements and thereby permit accurate tibial resection with a single surgical saw cut. The tibial prothesis component can thereafter be installed quickly and easily and in a securely seated position.

As shown in FIGS. 1 and 2, the tibial cutting jig 10 of the present invention requires preinstallation of an intramedullary alignment rod 16 of the type known for use in total knee prothesis surgery. This intramedullary rod 16 is installed by initially drilling and then reaming a passage 20 extending into the upper or proximal end of the tibial plateau 18. This drilling and reaming procedure is performed with the knee joint operatively exposed and hyperextended to displace the lower or distal end of the femur 22 in an out-of-the-way position, as viewed in FIG. 2. The intramedullary rod 16 is then installed to extend generally along the longitudinal axis by sufficient insertion, for example, of the rod 16 to extend into and/or through the isthmus region of the tibia 14. When inserted, the upper end of the intramedullary rod 16 extends upwardly a short distance above the tibial plateau 18.

The cutting jig 10 is formed from an appropriate surgical material such as stainless steel or the like to include a base 24 with an upright or vertical bore 26 sized for close sliding reception of the upper end of the intramedullary rod 16. As shown in FIGS. 2 and 3, the base 24 supports laterally outwardly projecting outrigger pins 28 which are suitably anchored into the base as by press fitting or the like. As shown in the exemplary drawings, the preferred form of the invention includes two vertically spaced and generally parallel outrigger pins 28 on each side of the base 24.

The outrigger pins 28 are adapted to receive measurement keys 30 for spacing the entire jig 10 at a vertical position referenced directly from the tibial plateau 18. More particularly, the measurement keys 30 are provided in pairs of different sizes, with each key 30 having a pair of vertically spaced openings 32 therein for sliding reception onto an associated pair of the outrigger pins 28. The lower end of each key 30 is tapered to a relatively blunt tip 34 for contacting the tibial plateau 18, whereas the upper end of each key 30 conveniently bears indicia 36 representing the size of the key, as will be described in more detail.

The cutting jig base 24 also supports the saw guide 12 by means of an extension 38 which protrudes anteriorly and depends from the base 24. The saw guide 12 is carried at the lower end of the extension 38 and conventionally includes horizontal guide plates 40 separated by a vertical median 42 to define a pair of laterally opening saw guide slots 44. These slots 44 are dimensioned to receive the blade 46 of a surgical saw 48 such as a traditional oscillating power saw or the like to guide the saw blade 46 into the desired cutting relation with the patient's tibia 14.

As shown in FIGS. 2 and 3, the vertical location of the saw guide 12 is referenced directly from the tibial plateau 18 by a dimension selected according to the sizes of the selected measurement keys 30. Alternately stated, the measurement keys 30 control the vertical position of the jig base 24 above the tibial plateau and thus also control the vertical position of the saw guide slots 44 which are positioned slightly below the tibial plateau. The precise spacing of the saw guide slots 44 below the tips 34 of the measurement keys 30 is represented by the indicia 36 on the keys, wherein this dimension is selected according to the individual patient and according to the implant design and size to be used. While measurement keys 30 providing a 10 mm spacing are shown in the drawings, alternative keys having alternative spacings such as 7 mm or 8 mm or other sizes can be used as required.

With the cutting jig 10 installed onto the intramedullary rod 16 by use of the selected measurement keys 30, the base 24 of the jig 10 is preferably locked in position by a set screw 50 threaded into the base and having a shank for bearing tightly against the rod 16. With the base 24 locked in place, the surgeon can then quickly and easily perform the desired resection of the tibia 14 using the power saw 48 to cut a thin wafer from the tibial plateau 18. After resection, the cutting jig 10 is removable quickly and easily by loosening the set screw 50, after which the intramedullary rod 16 is removed. This leaves the resected tibial surface 52 exposed as shown in FIG. 4 for facilitated mounting of the tibial component of a total knee prosthesis. While the cutting jig 10 of the present invention may be used with a variety of different total knee prostheses, the invention is particularly adapted for use with the Whiteside total knee system marketed by Dow Corning Wright of Arlington, Tenn. under the name ORTHOLOC.

The improved cutting jig 10 of the present invention thus provides means for obtaining accurate tibial resection along a cutting plane referenced directly and at a vertically selected distance from the tibial plateau. Potentially inaccurate measurements referenced from other points, such as referenced from an intramedullary rod, are thus avoided. Moreover, the direct contact of the keys 30 with the tibial surface prevents settling of the intramedullary rod which can otherwise cause inaccurate measurements and resultant inaccurate cutting.

A variety of modifications and improvements to the invention described herein are believed to be apparent to those of ordinary skill in the art. Accordingly, no limitation on the invention is intended by way of the description and accompanying drawings, except as set forth in the appended claims.

What is claimed is:

1. A tibial cutting jig for use in resection of the tibia of a patient having an intramedullary alignment rod projecting upwardly from the tibial plateau generally along a longitudinal axis of the tibia, said cutting jig comprising:

a base for reception over the intramedullary rod;

outrigger pins projecting laterally outwardly in opposite directions from said base;

measurement keys for removable mounting onto said outrigger pins, said measurement keys having lower tips at predetermined distances below said base; and a saw guide depending from said base and including at least one saw guide slot disposed below said lower tips of said measurement keys when said keys are carried by said outrigger pins.

2. The tibial cutting jig of claim 1 wherein said measurement keys bear indicia representing the dimensional spacing of said saw guide slot below the lower tips of said keys.

3. The tibial cutting jig of claim 1 further including a plurality of pairs of said measurement keys, each pair of said measurement keys having lower tips at a different predetermined distance below said base.

4. The tibial cutting jig of claim 3 wherein each of said pairs of said measurement keys bears indicia representing the dimensional spacing of said saw guide slot below said lower tips of said measurement keys.

5. The tibial cutting jig of claim 1 wherein a pair of said outrigger pins projects laterally outwardly from each of the opposite sides of said base, and further wherein each of said measurement keys has a pair of openings formed therein for sliding reception onto the pair of said pins on one of the sides of said base.

6. The tibial cutting jig of claim 1 further including means for releasably locking said base onto the intramedullary rod.

7. The tibial cutting jig of claim 6 wherein said locking means comprises a set screw threadably carried by said base.

8. The tibial cutting jig of claim 1 further including an extension projecting anteriorly and depending from said base, said saw guide being carried by said extension.

9. The tibial cutting jig of claim 8 wherein said saw guide slot includes a pair of saw guide slots oriented generally in a common plane disposed generally perpendicular to the tibial longitudinal axis.

10. A tibial cutting jig for use in resection of the tibia of a patient having an intramedullary alignment rod projecting upwardly from the tibial plateau generally along a longitudinal axis of the tibia, said cutting jig comprising:
  a base for reception over the intramedullary rod and including means for releasably locking said base with respect to said intramedullary rod;
  a pair of outrigger pins projecting laterally outwardly and generally in parallel from each of the laterally opposite sides of said base;
  a plurality of pairs of measurement keys for removable mounting onto the outrigger pins on said base, each of said keys having a pair of openings formed therein for sliding reception of said pins, and each pair of said measurement keys having lower tips at a predetermined distance below said base, said predetermined distance for each of said pairs of said keys being different from the remaining pairs of said keys; and
  a saw guide depending from said base on the anterior side thereof and having at least one saw guide slot formed therein at a position disposed below said lower tips of the measurement keys on said outrigger pins, said measurement keys having indicia thereon representing the dimensional spacing between said lower tips and said saw guide slot.

11. The tibial cutting jig of claim 10 wherein said outrigger pins on each side of said base are vertically spaced from one another.

12. A tibial cutting jig assembly for use in resection of the tibia of a patient, said assembly comprising:
  an intramedullary alignment rod for installation into the tibia to project upwardly therefrom generally along the longitudinal axis of the tibia;
  a jig base having a vertical bore formed therein for reception over said rod;
  outrigger means projecting laterally outwardly from opposite lateral sides of said base;
  saw guide means depending from the anterior side of said base and including at least one saw guide slot formed therein; and
  key means for removable reception onto said outrigger means and including lower tips for directly contacting the tibia and for spacing said base above the tibia, said key means being provided in different sizes for spacing said base above the tibia by different distances to correspondingly select the vertical position of the saw guide slot relative to the tibia.

13. The tibial cutting jig assembly of claim 12 wherein each of said keys bears indicia representing the size thereof.

* * * * *